US011109775B2

(12) United States Patent
Klinder et al.

(10) Patent No.: US 11,109,775 B2
(45) Date of Patent: Sep. 7, 2021

(54) SHAPE SENSING ASSISTED MEDICAL PROCEDURE

(71) Applicant: KONINKLIJKE PHILIPS N.V., Eindhoven (NL)

(72) Inventors: Tobias Klinder, Uelzen (DE); Bharat Ramachandran, Morganville, NJ (US); Robert Manzke, Bonebuttel (DE); Raymond Chan, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1221 days.

(21) Appl. No.: 14/349,358

(22) PCT Filed: Oct. 8, 2012

(86) PCT No.: PCT/IB2012/055415
§ 371 (c)(1),
(2) Date: Apr. 3, 2014

(87) PCT Pub. No.: WO2013/057620
PCT Pub. Date: Apr. 25, 2013

(65) Prior Publication Data
US 2014/0243660 A1    Aug. 28, 2014

Related U.S. Application Data

(60) Provisional application No. 61/549,281, filed on Oct. 20, 2011.

(51) Int. Cl.
*A61B 5/06* (2006.01)
*A61B 34/20* (2016.01)
(Continued)

(52) U.S. Cl.
CPC ............ *A61B 5/066* (2013.01); *A61B 1/2676* (2013.01); *A61B 5/065* (2013.01); *A61B 5/6847* (2013.01);
(Continued)

(58) Field of Classification Search
CPC ..... A61B 5/00; A61B 34/10; A61B 2034/107; A61B 34/20; A61B 2034/2061
See application file for complete search history.

(56) References Cited

U.S. PATENT DOCUMENTS

| 5,274,551 A | 12/1993 | Corby |
| 7,756,563 B2 | 7/2010 | Higgins |

(Continued)

FOREIGN PATENT DOCUMENTS

| WO | WO 2010076675 A1 * | 7/2010 | ......... A61B 17/3421 |
| WO | WO2010111090 | 9/2010 | |
| WO | WO2012131550 | 10/2012 | |

*Primary Examiner* — Angela M Hoffa

(57) ABSTRACT

A system and method for shape sensing assistance in a medical procedure includes a three-dimensional image (111) of a distributed pathway system (148). A shape sensing enabled elongated device (102) is included for insertion into the pathway system to measure a shape of the elongated device in the pathway system. A pathway determination module (144) is configured to compute a planned path to a target in the three-dimensional image and compute permissible movements of the elongated device at diverging pathways in the pathway system to provide feedback for deciding which of the diverging paths to take in accordance with the planned path.

14 Claims, 4 Drawing Sheets

(51) Int. Cl.
*A61B 5/00* (2006.01)
*A61B 6/12* (2006.01)
*A61B 1/267* (2006.01)
*A61B 90/00* (2016.01)
*A61B 34/10* (2016.01)

(52) U.S. Cl.
CPC ............ *A61B 5/742* (2013.01); *A61B 5/7405* (2013.01); *A61B 5/7455* (2013.01); *A61B 6/12* (2013.01); *A61B 34/20* (2016.02); *A61B 90/03* (2016.02); *A61B 2034/107* (2016.02); *A61B 2034/2061* (2016.02)

(56) References Cited

U.S. PATENT DOCUMENTS

| | | |
|---|---|---|
| 8,864,655 B2 | 10/2014 | Ramamurthy et al. |
| 2004/0097805 A1 | 5/2004 | Verard et al. |
| 2005/0182319 A1* | 8/2005 | Glossop .................. A61B 5/20 600/424 |
| 2007/0055128 A1 | 3/2007 | Glossop |
| 2007/0167714 A1 | 7/2007 | Kiraly |
| 2008/0183073 A1* | 7/2008 | Higgins ................ A61B 6/032 600/425 |
| 2008/0218770 A1 | 9/2008 | Moll et al. |
| 2009/0137952 A1* | 5/2009 | Ramamurthy ....... A61B 5/4887 604/95.01 |
| 2010/0030063 A1 | 2/2010 | Lee et al. |
| 2010/0099951 A1 | 4/2010 | Laby et al. |
| 2010/0249506 A1* | 9/2010 | Prisco ................ A61B 1/00059 600/117 |
| 2011/0319910 A1* | 12/2011 | Roelle ............... A61B 19/2203 606/130 |
| 2012/0157834 A1* | 6/2012 | Lazebnik ............ A61B 8/0841 600/437 |
| 2012/0289777 A1* | 11/2012 | Chopra ............. A61B 5/02028 600/109 |

\* cited by examiner

SHAPE SENSING ASSISTED MEDICAL PROCEDURE

CROSS-REFERENCE TO PRIOR APPLICATIONS

This application is the U.S. National Phase application under 35 U.S.C. § 371 of International Application Serial No. PCT/IB2012/055415, filed on Oct. 8, 2012, which claims the benefit of U.S. Application Ser. No. 61/549,281, filed on Oct. 20, 2011 and published as U.S. Patent Application Publication No. 2014243660. These applications are hereby incorporated by reference herein.

RELATED APPLICATION DATA

This application is related to commonly assigned U.S. Patent Application Publication No. 2014039306, having a priority date of Mar. 31, 2011 and incorporated herein by reference.

This disclosure relates to shape sensing assisted procedures and more particularly to systems and methods utilizing shape sensing data to navigate complex biological or mechanical systems.

Diagnostic bronchoscopy is the process of inserting a rigid or flexible endoscope into the airways via the mouth to obtain a biopsy. The biopsy can be performed to confirm cancer, identify a type of cancer, stage for cancer, determine an effect of therapy, etc. During an intervention, a bronchoscope is inserted in the airways, and the pulmonologist navigates to a target. However, taking tissue samples during a bronchoscopy is a difficult task with a lower than desired rate of successful procedures due to several reasons. First, the topology of the airways is very complex, and the physician may get lost advancing a scope down the bronchial tree. Second, in a peripheral region, a size of the bronchoscope may be larger than the diameter of the airways, and the physician no longer receives image feedback from the bronchoscope. In addition, while attempting to navigate to a target, a pneumothorax or collapsed lung may result.

Pre-operative imaging data, such as a computed tomography (CT) scan of the chest and lungs, provides a valuable source of information even though the patient's anatomy undergoes deformation due to different positioning in an interventional suite, e.g., due to the CT scan, patient motion, respiratory motion, etc. Despite positional changes, the topology of the airway tree remains relatively unchanged. To assist navigation, different approaches have been proposed; however, accurate and reliable targeting remains a significant problem, especially for targets in the peripheral region of the lung.

In accordance with the present principles, a system and method for shape sensing assistance in a medical procedure include a planned pathway to a target through a three-dimensional image of a distributed pathway system. A shape sensing enabled elongated device is introduced into the pathway system, and a shape of the elongated device in the pathway system is measured. The shape of the elongated device is compared with a shape of the planned pathway in the three-dimensional image to determine a location of the elongated device on the planned pathway. Permissible movements of the elongated device are determined at diverging pathways to maintain the elongated device on the planned pathway.

A system and method for shape sensing assistance in a medical procedure include a three-dimensional image of a distributed pathway system. A shape sensing enabled elongated device is included for insertion into the pathway system to measure a shape of the elongated device in the pathway system. A pathway determination module is configured to compute a planned path to a target in the three-dimensional image and compute permissible movements of the elongated device at diverging pathways in the pathway system to provide feedback for deciding which of the diverging paths to take in accordance with the planned path.

Another system includes a processor and a memory device coupled to the processor and configured to store a three-dimensional image of a distributed pathway system, and a pathway determination module configured to compute a planned path to a target in the three-dimensional image. A shape sensing enabled elongated device is included for insertion into the pathway system to measure a shape of the elongated device in the pathway system. The pathway determination module is configured to compute permissible movements of the elongated device at diverging pathways in the pathway system. A feedback mechanism is configured to provide sensory feedback for deciding which of the diverging paths to take in accordance with the planned path.

These and other objects, features and advantages of the present disclosure will become apparent from the following detailed description of illustrative embodiments thereof, which is to be read in connection with the accompanying drawings.

BRIEF DESCRIPTION OF THE DRAWINGS

This disclosure will present in detail the following description of preferred embodiments with reference to the following figures wherein.

DETAILED DESCRIPTION

Figure 1:
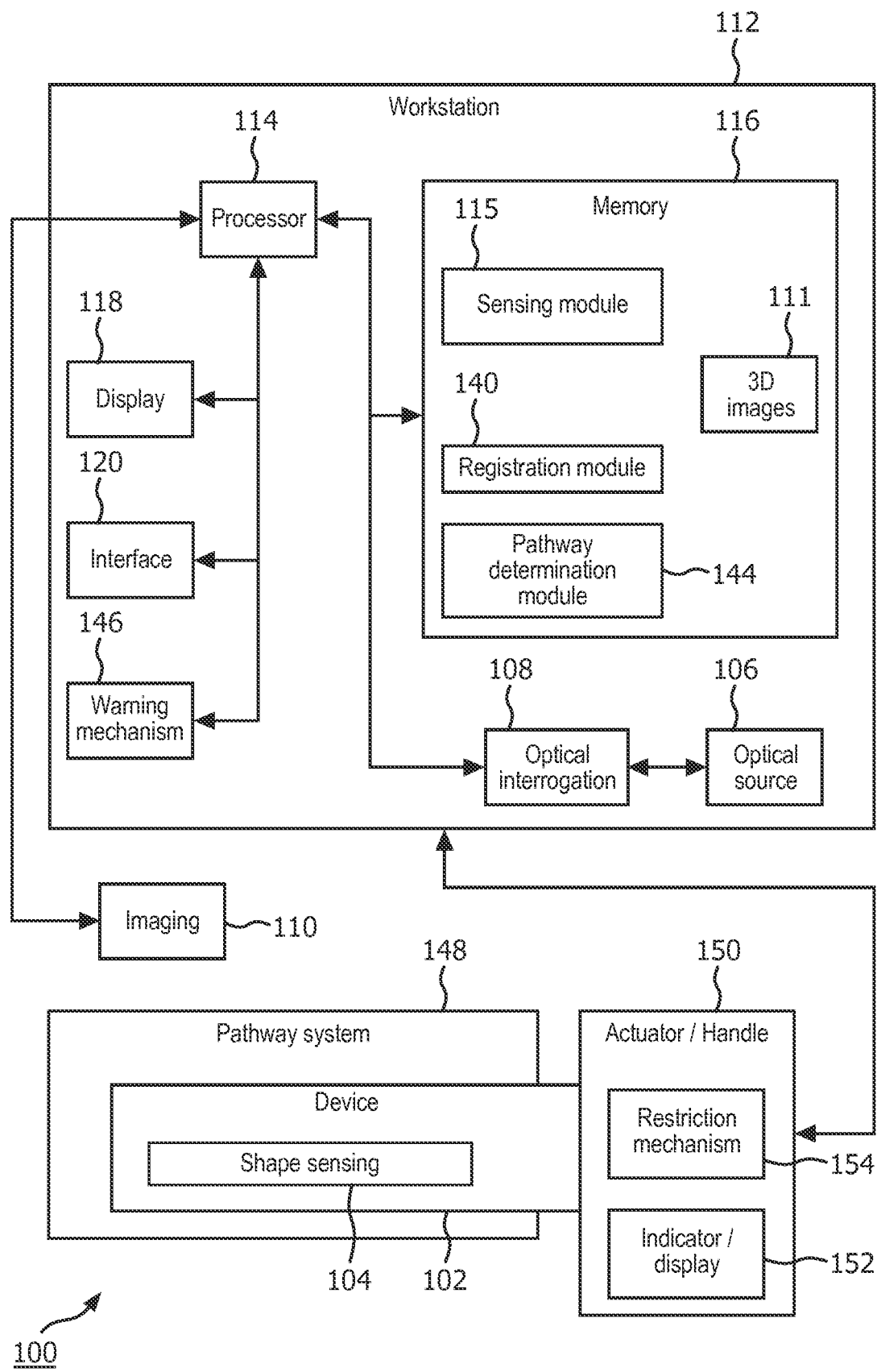
FIG. 1 is a block/flow diagram showing a system/method for shape sensing assistance in a medical procedure in accordance with the present principles.

In accordance with the present principles, device navigation is improved during a procedure by extracting shape-sensing data of a device and restricting the shape of the device based on a planned path using pre-operative data. The device may include, e.g., a bronchoscope, guide sheath, catheter or other instrument. The navigation is guided by the plan, which results in a faster and more accurate navigation with more reliable targeting and lower risk of negative consequences, such as, e.g., pneumothorax in a bronchoscopy application.

In a particularly useful embodiment, a system collects shape sensing information (e.g., optical shape sensing) to verify actual bronchoscope paths relative to target paths planned from pre-operative imaging data. The system includes a shape sensing enabled endoluminal device, e.g., bronchoscope, guide sheath, etc. Pre-operative imaging data, such as computed tomography (CT) scan images are provided. Multimodality processing methods may be employed to fuse images with shape sensing. A path planning algorithm provides a navigation plan based on the pre-operative data. As the device is advanced, restrictions are checked against the planned path. The shape is evaluated according to the path-planning. If a violation or an incorrect path is taken, real-time visual or sensory feedback is generated, e.g. haptic feedback, etc., to permit correction by a physician so that the planned path can be followed.

Tracking technology permits reconstruction of device shapes along a length of the device. The shape-sensed data and tracked position are then correlated with previously collected images. With shape sensing, three-dimensional (3D) information of the shape of the device (thus 3D information, e.g., compared to 2D information provided by X-ray or sparse 3D point information from electromagnetic tracking) is available. This shape information is of particular interest in complex systems, such as the airways in lungs, where the shape information can be employed to assist a physician to validate whether a correct path has been selected. Furthermore, sensors may be attached to the device and can account for deformations caused by breathing or heart beat so that this motion can be compensated.

Shape information can be derived from a variety of systems. These include: optical shape interrogation systems (e.g., fiber optic Bragg sensors, Rayleigh scattering, Brillouin scatter, optical intensity-based attenuation), multi-coil arrays for electromagnetic (EM) localization of points on an apparatus, laser scanning systems for three-dimensional surface estimation and optical/acoustic marker/emitter arrays for camera (time-of-flight or conventional optical measurement) or microphone-based interrogation of shape. Real-time imaging such as ultrasound may also be used for shape information.

In one illustrative example, during a bronchoscopic procedure, a physician may attempt to reach a target with a bronchoscope that is inserted through the airways of the lungs. The topology of the airways is very complex which often causes physicians to navigate incorrect paths. Even if pre-operative imaging data is available for guidance, deformations due to breathing or patient repositioning compromise successful targeting. The present principles employ shape sensing information obtained from the bronchoscope to reconstruct bronchoscope shapes along whole instrument lengths. This information can be used to overcome current limitations in bronchoscopic interventions by permitting a check between correct and incorrect device shapes which indicate correct or incorrect pathways to a target. In addition, computational comparisons between a planned path and an actual shape of the shape sensed device are performed. If an incorrect path is taken, the physician is immediately warned to permit correction.

It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-RAY) and DVD.

Referring now to the drawings in which like numerals represent the same or similar elements and initially to FIG. 1, a system 100 for performing a medical procedure is illustratively depicted. System 100 may include a workstation 112 from which a procedure is supervised and managed. Workstation 112 preferably includes one or more processors 114 and memory 116 for storing programs and applications. Memory 116 may store a sensing module 115 configured to interpret feedback signals from a shape sensing device 104. In one embodiment, sensing module 115 is configured to use optical signal feedback (and any other feedback, e.g., electromagnetic (EM)) from shape sensing device 104 to reconstruct deformations, deflections and other changes associated with a medical device 102 and/or its surrounding region. The medical device 102 is preferably elongated and may include, e.g., a catheter, a guide wire, an endoscope, a probe, a robot, an electrode, a filter device, a balloon device, or other medical component, etc. Workstation 112 may include a display 118 for viewing internal images of a subject if an imaging system 110 is employed. The imaging system 110 may include, e.g., a magnetic resonance imaging (MRI) system, a fluoroscopy system, a computed tomography (CT) system, ultrasound (US), etc. Display 118 may also permit a user to interact with the workstation 112 and its components and functions. This is further facilitated by an interface 120 which may include a keyboard, mouse, a joystick or any other peripheral or control to permit user interaction with the workstation 112.

Workstation 112 may include an optical source 106 to provide optical fibers with light when shape sensing device 104 includes optical fiber shape sensing. An optical interrogation unit 108 may also be employed to detect light returning from all fibers. This permits the determination of strains or other parameters, which will be used to interpret the shape, orientation, etc. of the medical device 102, which may be interventional. The light signals will be employed as feedback to make adjustments to access errors and to calibrate the medical device 102 or system 100.

Shape sensing device 104 preferably includes one or more fibers which are configured to exploit their geometry for detection and correction/calibration of a shape of the medical device 102. Optical interrogation unit 108 works with sensing module 115 (e.g., shape determination program) to permit tracking of instrument or medical device 102.

Imaging system 110 may be provided for collecting pre-operative imaging data or real-time intra-operative imaging data. The pre-operative imaging may be performed at another facility, location, etc. in advance of any procedure. These images 111 may be stored in memory 116, and may include pre-operative 3D image volumes of a patient or pathway system. The pathway system may, for example, be a lung or may, as a further example, be a gastro-intestinal tract, excretory organs, blood vessels, body lumen or other part of a patient's anatomy.

In a particularly useful embodiment, medical device 102 is employed to discover or observe a target. The target may include a lesion, tumor, injury site, object or other target. During the procedure, shape sensing data from shape sensing device 104 is collected and registered with the pre-operative imaging data. A registration module 140 determines registration positions and registers the shape sensing data with the pre-operative images 111, which are preferably 3D images. The registration module 140 may employ multimodality processing methods (e.g., to process more than one source of imaging data) to fuse imaging data with shape sensing data. The shape sensing data may include motion data from a heartbeat and/or breathing, and motion compensation may be performed to account for the same in the images (e.g., deformations due to breathing can be measured using shape sensing). The 3D images 111 may include these motion compensated images.

A pathway determination module 144 computes paths and compares rich point data from shape sensing data registered with the motion compensated images to determine a planned path to a target. In addition, the pathway determination module 144 monitors shape sensing data from the sensing module 115 to determine a current path being taken by the medical device 102 and to compare the current path with a correct path along the planned pathway. The position and the shape of the medical device 102 are compared with the motion compensated images by matching pathways, e.g., in the lungs, with the shape of the medical device 102. If lumen walls appearing along a planned path do not match the shape sensing data positions then a wrong path has been taken.

When a wrong path has been taken or about to be taken, the system 100 provides feedback to the clinician or physician. The feedback may take a plurality of different forms. For example, a visualization may be provided on display 118 which provides feedback to the physician that a wrong path was traversed and where the mistake most probably occurred to take corrective measures. Another embodiment provides an audible alarm or haptic feedback (e.g., device vibrates, etc.) when an incorrect path has been taken. The feedback may be provided before an incorrect path is taken as well.

System 100 may include a warning mechanism 146 configured to indicate that an incorrect path has been selected or is being selected. The warning mechanism 146 may take many forms and may be included in components that are already a part of the system 100 including mounted on medical device 102. The warning mechanism 146 may include one or more of the following features. The display 118 may be employed to display a location where the incorrect path was selected so that a physician can go back and make corrections. In addition or alternatively, a visual (display 118), haptic and/or audible (e.g., a speaker at interface 120) indicator may be generated when an incorrect path is selected. The warning mechanism 146 may be employed to warn of an imminent incorrect selection to effectively guide the physician during a procedure.

Pre-operative images 111, such as diagnostic volumetric CT images acquired before the procedure, serve as a "road map" for the procedure and provide very detailed information of the patient's anatomy. These images 111 are employed for planning, e.g., to define the optimal path along airways of a lung, for example, to reach the desired target. In the present embodiments, the images 111 are also employed for tracking the medical device 102 and its progress through a pathway system 148, such as a lung.

Even experienced physicians find it difficult to manipulate current bronchoscopes or medical devices 102, especially when they are inserted deep to access peripheral airways. Current bronchoscopes permit rotation of the whole bronchoscope and permit bending the tip. Using a shape sensing enabled bronchoscope/guide sheath/medical device 102, the three-dimensional shape of the scope can be measured in real-time while navigating along the airways of the lung.

Leveraging the shape information of shape sensing device 104 together with detailed information derived from pre-operative data (images 111), the medical device 102 (e.g., an endoluminal device) is restricted only to certain configurations that are consistent with the pre-operative CT image and the plan based on these images. This simplifies decision making for the physician whenever a bifurcation is reached. By restricting the shape in which the bronchoscope/guide sheath/medical device 102 can be inserted, chances of the pulmonologist entering a wrong airway or puncturing an incorrect airway wall and causing a pneumothorax are minimized.

A restriction of the shape according to the path-planning may be implemented in a plurality of ways. With the information derived from the pre-operative images 111 and the information from shape sensing device 104, a current shape of the medical device 102 can be monitored to restrict its shape, position or movement during navigation. For example, when reaching a bifurcation, an option is presented as to which way to turn. Once the shape sensing device 104 is registered with a pre-operative planning path from the pathway determination module 144, a clear decision on which bifurcation option to take can be made to assist the navigation. It should be noted that optical fiber shape sensing device 104 provides better and more accurate registration as compared to other methods, e.g., electromagnetic (EM) based navigation. This is in part due to the fact that the shape sensing data is available over an entire length of the device (fiber) as opposed to just the tip or a few points for EM tracking.

In one useful embodiment, the medical device 102 includes a bronchoscope, the pathway system 148 being analyzed includes a lung, and the shape sensing device 104 includes optical shape sensing. The pre-operative images 111 are obtained by computed tomography (CT) although other imaging methods may be employed. A global structure of airways of the lung is extracted from the pre-operative images 111, and a path that is supposed to be chosen to reach a target is computed by the pathway determination module 144. This path provides information about which path is supposed to be taken by the physician—thus limiting the possibilities where the bronchoscope can be.

In one embodiment, the pathway determination module 144 is configured to compute undesired angles or other impermissible movements for the shape sensing enabled medical device 102 to avoid taking an incorrect bifurcation option. By restricting the shape of the medical device 102 to only those movements that point in the direction of the desired bifurcation, navigation can clearly be improved.

In addition to determining the correct pathway, real-time visual or sensory feedback can be provided to assist a physician, e.g., haptic feedback. Shape restriction can be performed using different methods based on the feedback from shape sensing device 104 in combination with imaging data. In one embodiment, a tip actuator or handle 150 can have indicator lights or a display 152 to inform the operator how much and in which direction to deflect/rotate/advance/retract. The indicator lights may provide clues as to a correct motion to impart to the handle 150 to select a correct path. In another embodiment, the tip actuator or handle 150 may include a mechanism or mechanisms 154 to restrict actuation of the medical device 102 to a limited interval to assist in selecting a correct path. The mechanism 154 may be responsive to feedback that an incorrect path has been taken and restrict motion or indicate that motion should be ceased until a correction is made. In addition, steps or corrective measures may be indicated on the handle 150 or on a display 118. The mechanism 154 may include a gripping force or other mechanism to clamp on or otherwise restrict movement of the medical device 102. The mechanism 154 may work in conjunction with the warning mechanism 146 to provide visual or sensory indications to the physician.

Figure 2:
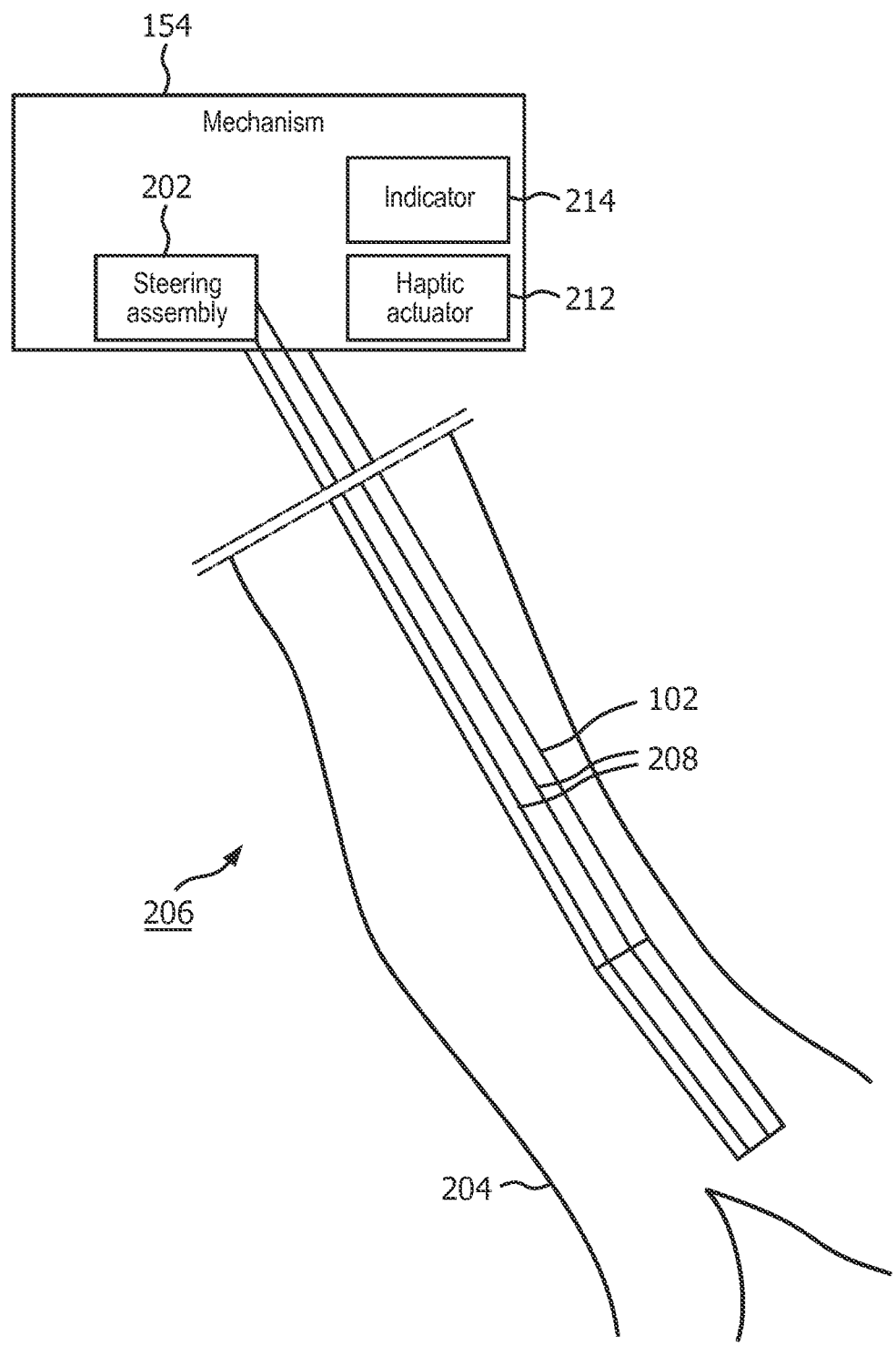
FIG. 2 is a diagram showing a scope at a bifurcated structure determining a correct path in accordance with one embodiment.

Referring to FIG. 2, in another embodiment, the medical device 102 includes a bronchoscope, which may have a manually or automatically controlled steering assembly 202 whose range of tip deflection and rotation can be set manually or programmatically based on information about a current tip position and shape (from shape sensing device 104) relative to a desired targeted path (from pathway determination module 144) within a branching structure (e.g., a bifurcation) 204 of a lung 206. In such an instance, range of motion limits can be implemented using an addressable actuation device 208. In this instance, "addressable" can mean capable of controlling the configuration of the medical device 102 using shape information and control signals or device settings. The addressable actuation device 208 may include electromechanical, electromagnetic, pneumatic (miniature bellows) or hydrodynamic (miniature fluid pistons) constraint components in the controlled steering assembly 202 that permit unconstrained motion of the tip by the operator when inside the boundaries that are dynamically computed from real-time imaging, shape sensing measurements, and path plan.

In one embodiment, close to the boundary constraints, sensory/haptic feedback is provided to the operator, e.g., by imposing mechanical resistance, increasing the friction on pullwires or by imparting force to counteract the operator motion. The sensory feedback may be provided by, e.g., a haptic actuator 212 to vibrate a device handle, visual and/or audible feedback (e.g., using warning mechanism 146 (FIG. 1)), display 118, a speaker at interface 120, indicators 214 (e.g., light emitting diodes, etc.) on the handle, etc. At a boundary constraint, constraint components or mechanism 154 and/or the addressable actuation devices 208 impart a full stop to the operator motion (using gripping or clamping devices or other stopping mechanisms (not shown)) so that the operator cannot deviate far from the path plan. The medical device 102 may be automated for computer-control of one or more degrees of freedom to simplify operator workflow. The device may be advanced and guided using computer controls by employing shape sensing data and pre-operative pathway data as described.

Figure 3:
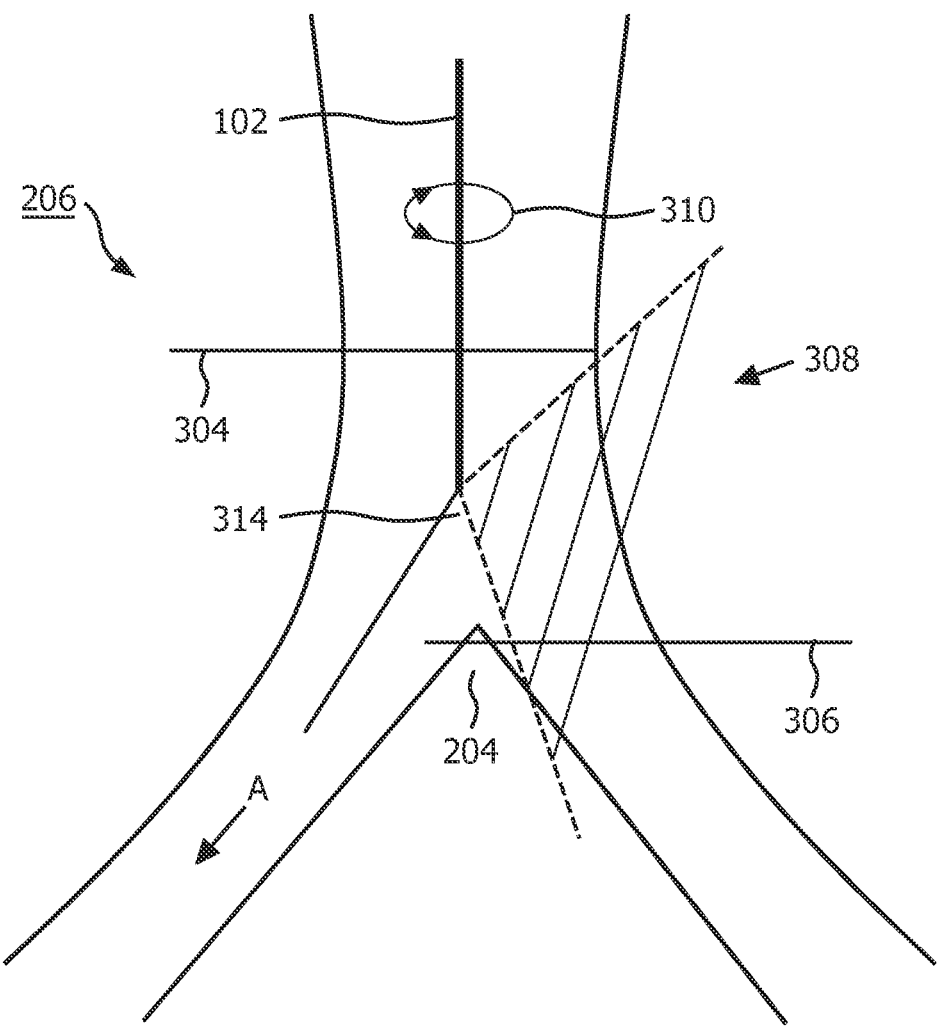
FIG. 3 is a diagram showing a bifurcated structure with an elongated device having impermissible movements computed in accordance with another embodiment.

Referring to FIG. 3, a view of the lung 206 includes the bifurcation 204 to be navigated by medical device 102. The medical device 102 may have upper limits 304 and lower limits 306, angular limits 308, rotational limits 310, etc. on the constraints placed on control wires or other mechanisms to constrain one or more degrees of freedom of the medical device 102 or its tip. The constraints or impermissible movements (upper limits 304, lower limits 306, angular limits 308 and rotational limits 310) are computed based upon a current position of the medical device 102 and the planned pathway in the 3D image volume.

The imposed constraints limit the medical device 102 behavior so that only tip directions that are consistent with the path plan can be realized. In one particularly useful embodiment, the medical device 102 may be initialized at a plurality of positions. For example, an orientation of a tip 314 of the medical device 102 may be automatically set at every position in a branching structure (e.g., bifurcation 204) so that the tip 314 points in a direction of arrow "A" consistent with the pathway plan in this case and would need only minor adjustments by the operator as the probe or medical device 102 is advanced further towards a target.

By performing continuous registration, between the shape and pre-operative data, the position of the tip 314 of the medical device 102 can be accurately tracked. Having this information is useful in deciding at which bifurcation the medical device 102 is currently in to permit changes to the shape restrictions for that bifurcation and for subsequently encountered bifurcations.

Figure 4:
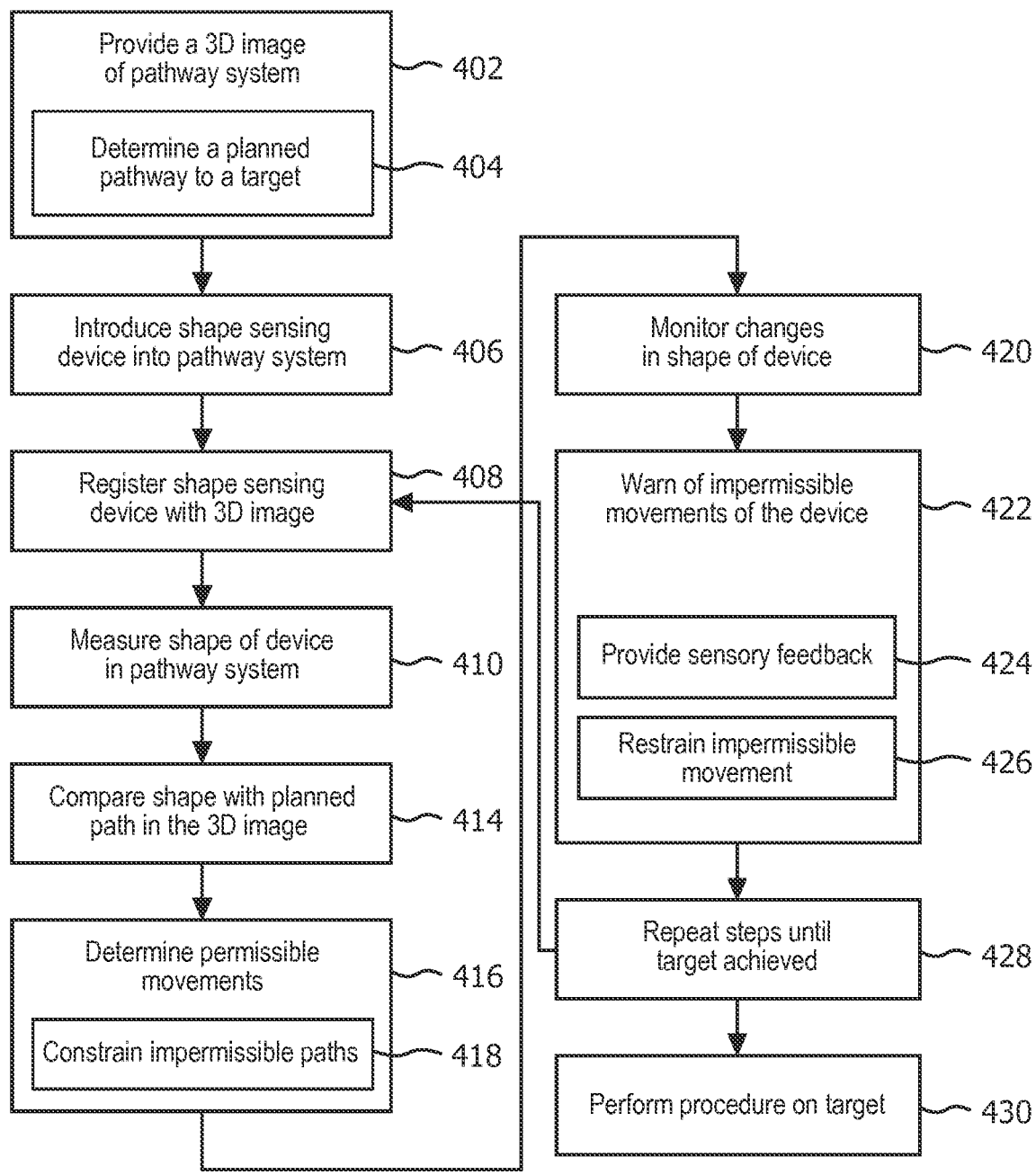
FIG. 4 is a block/flow diagram showing a method for shape sensing assistance in a medical procedure in accordance with illustrative embodiments.

Referring to FIG. 4, a method for providing shape sensing assistance in a medical procedure is illustratively shown in accordance with preferred embodiments. In block 402, a three-dimensional (3D) image of a distributed pathway system is provided. The 3D images may be created by segmenting CT images or images gathered through other systems or technologies (e.g., MRI, US, X-ray, etc.). The images may be processed for motion compensation or other corrections. The three-dimensional image may include a preoperative image volume. In block 404, a planned pathway is determined to a target through a three-dimensional image of a distributed pathway system.

In block 406, a shape sensing enabled elongated device is introduced into the pathway system. The pathway system may include a lung, a blood vessel, the heart, etc. The elongated device may include a medical device such as, e.g., a catheter, guide wire, bronchoscope, etc. The shape sensing is preferably performed using an optical fiber shape sensing system although other shape sensing devices may be employed.

In block 408, the elongated device is preferably registered with the three-dimensional image. This may be performed using a tracking system (e.g., EM), physical guide posts, a comparison between a sensed device shape and possible paths in the pathway system or other registration methods. In block 410, a shape of the elongated device is measured in the pathway system.

In block 414, the shape of the elongated device is compared with a shape of the planned pathway in the three-dimensional image to determine a location of the elongated device on the planned pathway. The target may include a lesion, tumor or other object of the procedure. In block 416, permissible movements of the elongated device are determined at diverging pathways to maintain the elongated device on the planned pathway. In block 418, constraints are placed on the movements which would result in an incorrect path being taken.

In block 420, changes in the shape of the elongated device are monitored. In block 422, a warning of impermissible movements is made if the shape is moved or occupies a position that has been deemed impermissible. In block 424, the warning may include sensory feedback such as, visual, haptic or audible feedback, indicating that an incorrect path was selected. In block 426, the elongated device may be restrained from impermissible movement. The restraints may include restricting advancement of the device, restricting steering of the device, restricting other controls or actions, etc.

In block 428, the process is repeated if necessary for each new decision (e.g., return to block 408) to reach the target. In block 430, a procedure is carried out with respect to the target.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for systems and methods for shape sensing assisted medical procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A method, comprising:
    determining a planned pathway in a biological body to a target through a three-dimensional image of a distributed pathway system in the biological body;
    introducing a shape sensing enabled elongated device into the distributed pathway system;
    measuring a shape of the elongated device in the distributed pathway system;
    comparing the shape of the elongated device with a shape of the planned pathway in the three-dimensional image to determine a location of the elongated device on the planned pathway;
    determining movements of the elongated device at branching pathways within the distributed pathway system to maintain the elongated device on the planned pathway, wherein the determining movements comprises computing constraints on the movements which result in a deviation from the planned pathway; and
    restraining the elongated device when the movements cause the elongated device to enter constrained areas automatically orienting a distal tip of the elongated device at at least one position in a branching of the distributed pathway system so that the distal tip points in a direction along the planned pathway.

2. The method as recited in claim 1, further comprising:
    monitoring changes in the shape of the elongated device; and
    warning a user when the movements cause the elongated device to enter the constrained areas.

3. The method as recited in claim 1, wherein restraining includes at least one of restricting advancement and restricting steering other than for the movements outside the constrained areas.

4. The method of claim 1, wherein the at least one position in the branching of the distributed pathway system comprises every position.

5. A system, comprising:
    a memory that stores a three-dimensional image of a distributed pathway system in a biological body and computer program code configured to compute a planned path to a target in the three-dimensional image;
    a shape sensing enabled elongated device for insertion into the distributed pathway system to measure a shape of the elongated device in the distributed pathway system;
    a hardware processor configured to execute the computer program code to compute a planned path in the biological body to a target in the three-dimensional image and to compute movements of the elongated device at diverging pathways in the distributed pathway system to provide feedback for deciding which of the diverging paths to take in accordance with the planned path; and
    a constraining mechanism comprising a steering assembly, a light, and a haptic actuator, wherein the constraining mechanism is coupled to the elongated device and configured to prevent the elongated device from selecting paths other than the planned path, and to orient automatically a distal tip of the elongated device at at least one position in a branching of the distributed pathway system so that the distal tip points in a direction along the planned path.

6. The system as recited in claim 5, wherein the memory further stores computer program code configured to register the elongated device with the three-dimensional image, executed by the hardware processor.

7. The system as recited in claim 5, further comprising a feedback mechanism comprising an indicator lights or a display, and configured to indicate that a path other than the planned path has been selected.

8. The system as recited in claim 7, wherein the feedback mechanism further comprises one of a haptic or audible indicator that a path other than the planned path has been selected.

9. The system as recited in claim 7, wherein the feedback mechanism further comprises an indicator to provide a direction for guiding movement of the elongated device.

10. The system as recited in claim 5, wherein the elongated device includes a medical device and the distributed pathway system includes a lung.

11. The system as recited in claim 10, wherein the three-dimensional image includes a preoperative image volume including the lung.

12. The system of claim 5, wherein the at least one position in the branching of the distributed pathway system comprises every position.

13. A system, comprising:
a memory device configured to store:
a three-dimensional image of a distributed pathway system in a biological body; and
computer program code configured to compute a planned path in the biological body to a target in the three-dimensional image;
a hardware processor configured to execute the computer program code;
a shape sensing enabled elongated device for insertion into the distributed pathway system to measure a shape of the elongated device in the distributed pathway system, the computer program code being configured to compute of the elongated device at diverging pathways in the distributed pathway system;
a constraining mechanism comprising a steering assembly, a light, and a haptic actuator, wherein the constraining mechanism is coupled to the elongated device and configured to prevent the elongated device from selecting paths other than the planned path, and to orient automatically a distal tip of the elongated device at at least one position in a branching of the distributed pathway system so that the distal tip points in a direction along the planned path; and
a feedback mechanism comprising indicator lights of a display, and configured to provide sensory feedback for deciding which of the diverging paths to take in accordance with the planned path.

14. The system of claim 5, wherein the at least one position in the branching of the distributed pathway system comprises every position.

* * * * *